(12) United States Patent
Moellmann

(10) Patent No.: US 7,098,447 B2
(45) Date of Patent: Aug. 29, 2006

(54) LIGHT SOURCE FOR THE ILLUMINATION OF MICROSCOPIC SPECIMENS AND SCANNING MICROSCOPE SYSTEM

(75) Inventor: Kyra Moellmann, Trippstadt (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 250 days.

(21) Appl. No.: 10/604,636

(22) Filed: Aug. 6, 2003

(65) Prior Publication Data

US 2004/0135079 A1 Jul. 15, 2004

(30) Foreign Application Priority Data

Aug. 6, 2002 (DE) ................. 102 35 914

(51) Int. Cl.
*G01J 5/02* (2006.01)
(52) U.S. Cl. .................. 250/234; 250/339.01
(58) Field of Classification Search ............ 250/234, 250/236, 338.5, 339.01, 339.06, 339.02, 250/339.05, 339.11, 458.1; 356/300; 422/82.05, 422/82.09; 436/164

See application file for complete search history.

(56) References Cited

U.S. PATENT DOCUMENTS

| | | | |
|---|---|---|---|
| 5,731,588 A | 3/1998 | Hell et al. | 250/458.1 |
| 6,356,088 B1* | 3/2002 | Simon et al. | 324/752 |
| 6,466,040 B1* | 10/2002 | Simon et al. | 324/752 |
| 6,608,295 B1* | 8/2003 | Engelhardt | 250/201.3 |
| 6,958,858 B1* | 10/2005 | Engelhardt et al. | 359/388 |
| 2002/0063220 A1 | 5/2002 | Engelhardt et al. | 250/458.1 |
| 2002/0074512 A1* | 6/2002 | Montagu et al. | 250/458.1 |
| 2002/0104961 A1* | 8/2002 | Hoffman | 250/234 |
| 2002/0109101 A1 | 8/2002 | Hoffmann | 250/458.1 |

\* cited by examiner

*Primary Examiner*—Georgia Epps
*Assistant Examiner*—Don Williams
(74) *Attorney, Agent, or Firm*—Simpson & Simpson, PLLC

(57) ABSTRACT

The present invention discloses a light source (10) for the illumination of microscopic specimens. The invention also discloses a scanning microscope system that possesses a light source (10). The light source (10) emits a combined light beam that is emitted by a first laser (4) and a second laser (6). In the combined light beam, the light of the first laser (4) is synchronized with the light of the second laser (6).

16 Claims, 2 Drawing Sheets

LIGHT SOURCE FOR THE ILLUMINATION OF MICROSCOPIC SPECIMENS AND SCANNING MICROSCOPE SYSTEM

CROSS REFERENCE TO RELATED APPLICATIONS

This patent claims priority of German patent application 102 35 914.8 which is incorporated by reference herein.

FIELD OF THE INVENTION

The invention concerns a light source for the illumination of microscopic specimens. Additionally, the invention concerns a scanning microscope system.

BACKGROUND OF THE INVENTION

The field of STED microscopy (for which see DE 44 16 558 C1 and DE 100 63 276 A1), two lasers are usually used, i.e. one to excite a sample region and another to generate the stimulated emission. Generating the stimulated emission, in particular, requires high light power levels and at the same time the greatest possible flexibility in wavelength selection. Optically parametric oscillators (OPOs) are often used for this. For efficient frequency conversion, it is useful to pump an OPO optically with a high-power laser. These are usually mode-coupled pulsed lasers, which as a rule are very expensive. There are also costs for the excitation light source, which normally also comprises a mode-coupled pulsed laser. All the lasers must furthermore be exactly aligned in order to strike the individual sample regions exactly. In the case of pulsed excitation, it is important to ensure that the light pulses generating the stimulated emission arrive within a specific time frame (which depends on the lifetime of the excited states of the sample material) after the excitation light pulses. Since the two laser sources are independent of one another, exact synchronization of the emitted laser pulses is necessary. Synchronization of the pulsed lasers with one another is usually achieved by means of an active control system. This is complex, and often unsatisfactory and unstable in operation.

German Patent Application DE 100 56 382 discloses a light source for illumination in scanning microscopy, and a scanning microscope. The light source and the scanning microscope contain an electromagnetic energy source that emits light of one wavelength, and a means for spatial division of the light into at least two partial light beams. An intermediate element for wavelength modification is provided in at least one partial light beam. The advantage of this arrangement is that the light pulses in the two partial light beams are always synchronized with one another. It is disadvantageous, however, that two partial light beams must be generated, thereby reducing the intensity in each of the partial beams. Since the power level of the electromagnetic energy source, which for example can be a Ti:sapphire laser, is split, insufficient power is often available for the application.

A passive synchronization of pulse trains coming from two different lasers is disclosed, for example, in W. Seitz et al., Opt. Lett. Vol. 27, No. 6, p. 454 (2002). This describes a method and an arrangement for passively synchronizing two completely different lasers (in the specific case a Ti:sapphire laser and a Nd:YVO$_4$ laser) with one another by optically modulating the intra-resonator losses of a slave laser (here the Nd:YVO$_4$ laser) by means of a master laser (here the Ti:sapphire laser). A Fabry-Perot mirror, comprising a semiconductor whose energy band boundary lies between the photon energies of the two lasers, is used for this. This method is particularly simple and practical compared to other synchronization methods. The document gives no indication, however, that the system can be used as a light source for microscopic examinations.

SUMMARY OF THE INVENTION

It is therefore the object of the invention to propose a light source for the illumination of microscopic specimens in which the lasers used can easily be synchronized.

This object is achieved by a light source for the illumination of microscopic specimens which comprises:
  a first and a second laser wherein each of which emits light into a first beam path and into a second beam path;
  an optical combining means being introduced in the first and in the second beam path; and
    a displaceable deflection unit for setting a path length difference between the light of the first and the second laser.

A further object of the invention is to propose a scanning microscope system that possesses a wide bandwidth of examination capabilities.

With regard to a scanning microscope system, the object is achieved by a scanning microscope having:
  a beam deflection device for guiding an illuminating light beam over a sample,
  a microscope optical system,
  a detector,
  a light source which emits a combined light beam that is generated by a first laser and a second laser; and
    an optical combining means which synchronizes the light of the first laser with the light of the second laser.

The invention has the further advantage that two different lasers can be synchronized. "Synchronization" here is understood to mean not only that the pulses of the two lasers overlap in time, but also that the pulses of the lasers arrive at the sample location in a specific chronological sequence. In addition, a measurement unit for ascertaining cross-correlation is provided, which receives a portion of the light of the first laser and a portion of the light of the second laser. The cross-correlation, which can be used for ascertaining a setting signal for adjusting the synchronization or controlled delay of the laser pulses of the first and/or second laser, is ascertained by summed frequency mixing in a nonlinear crystal. A displaceable deflection unit is provided for setting a path length difference between the light of the first and of the second laser. The result of this displacement can be checked using the measurement unit for ascertaining cross-correlation.

Utilization in a scanning microscope system having a beam deflection device for guiding an illuminating light beam over a sample is particularly advantageous. A microscope optical system and at least one detector are provided. Also provided in the scanning microscope system is a light source which emits a combined light beam that is emitted from a first laser and a second laser; and that in the combined light beam, the light of the first laser is synchronized with the light of the second laser.

BRIEF DESCRIPTION OF THE DRAWINGS

Further advantageous embodiments are evident from the dependent claims. The subject matter of the invention is

DETAILED DESCRIPTION OF THE INVENTION

Figure 1:
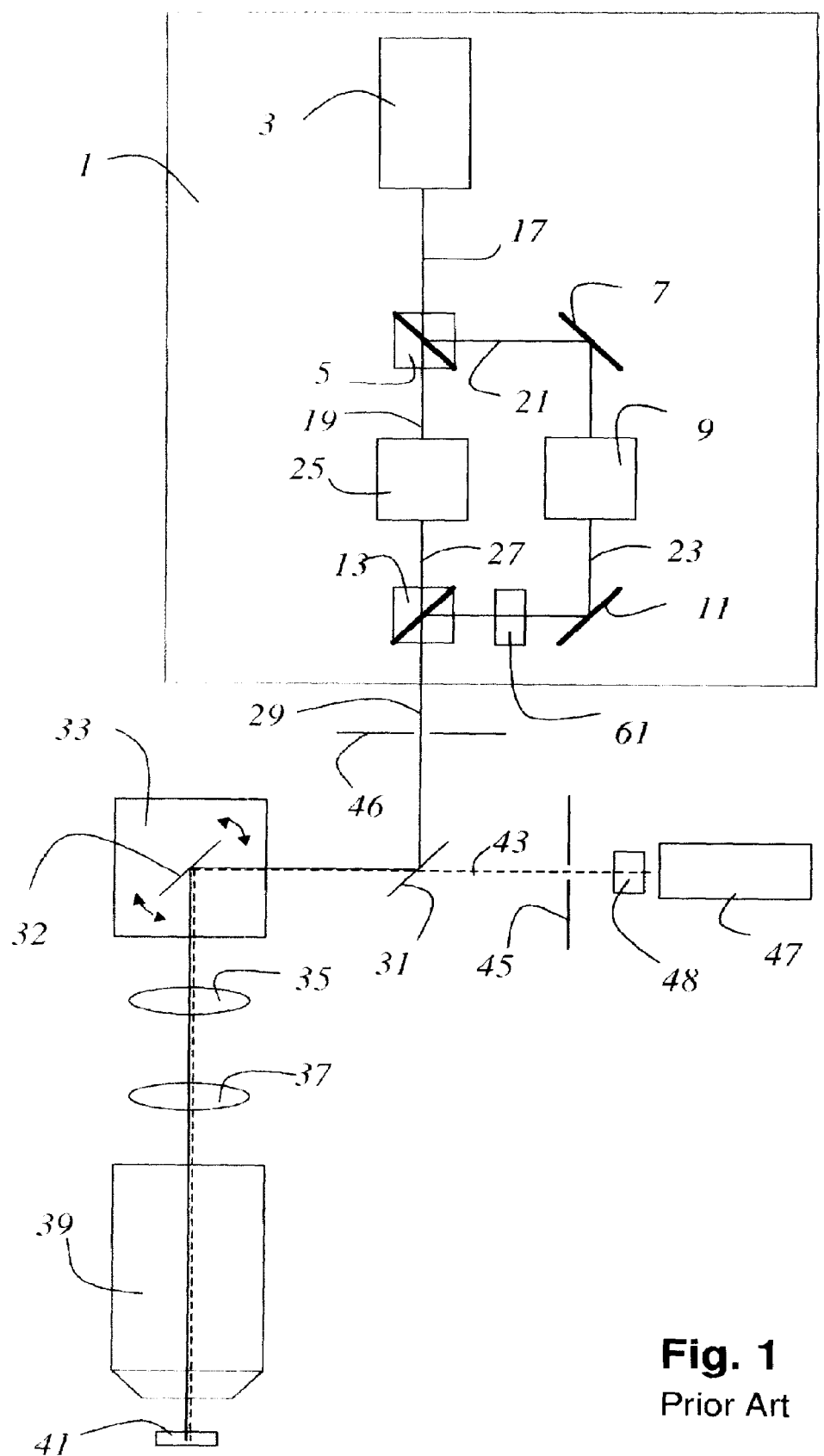
FIG. 1 shows a light source in combination with a scanning microscope, according to the existing art.

FIG. 1 shows a scanning microscope in combination with a light source 1 according to the existing art. A single pulsed laser, which is embodied as a titanium: sapphire laser, is provided as electromagnetic energy source 3. Light 17 of the pulsed laser is split into a first and a second partial light beam 19 and 21 using the means for spatial division of the light, which is embodied as beam splitter 5. Partial light beam 21 travels via mirror 7 to intermediate element 9, which is embodied as an optically parametric oscillator. Partial light beam 23 proceeding from optically parametric oscillator 9 is guided via mirror 11 to dichroic beam combiner 13, where it is combined with a partial light beam 19 to form illuminating light that emerges from light source 1. Mirrors 7 and 11 are tiltably mounted so that the relative positions of the components of the illuminating light are adjusted with respect to one another. Light source 1 is coupled to a scanning microscope. In the embodiment shown here, light source 1 contains in the beam path of partial light beam 23, in addition to an optically parametric oscillator 9, a means for influencing focus shape 61, which is embodied as a /2 plate and through which only the center portion of the cross-section of partial light beam 23 passes. Partial light beam 19 also arrives at an optically parametric oscillator 25. The partial light beam proceeding therefrom has a different wavelength, and is labeled 27. Partial light beam 23 that has passed through the λ/2 plate is guided to dichroic beam combiner 13, where it is combined with partial light beam 27 to form illuminating light 29 which emerges from light source 1.

Illuminating light 29 is reflected by a beam splitter 31 to beam deflection device 33, which contains a gimbal-mounted scanning mirror 32 that guides illuminating light 29 through scanning optical system 35, tube optical system 37, and microscope optical system 39 over or through sample 41. With non-transparent samples 41, illuminating light 29 is guided over the sample surface. In the case of biological samples (preparations) or transparent samples, illuminating light 29 can also be guided through sample 41. This means that from different focal planes of sample 41 are successively scanned by illuminating light 29 Illuminating light 29 is depicted as a solid line. Detected light 43 proceeding from the sample passes through microscope optical system 39 and via beam deflection device 33 to beam splitter 31, passes through the latter and strikes detector 47, which is embodied as a photomultiplier. Detected light 43 proceeding from sample 41 is depicted as a dashed line. In detector 47, electrical detected signals proportional to the power level of detected light 43 proceeding from the specimen are generated, and are forwarded to a processing unit (not depicted). A bandpass filter 48, which blocks out light of the wavelengths of partial light beams 23 and 27, is arranged in front of the detector. Illumination pinhole 46 and detection pinhole 45 that are usually provided in a confocal scanning microscope are drawn in schematically for the sake of completeness. Omitted in the interest of greater clarity, however, are certain optical elements for guiding and shaping the light beams. These are sufficiently familiar to one skilled in this art.

Figure 2:
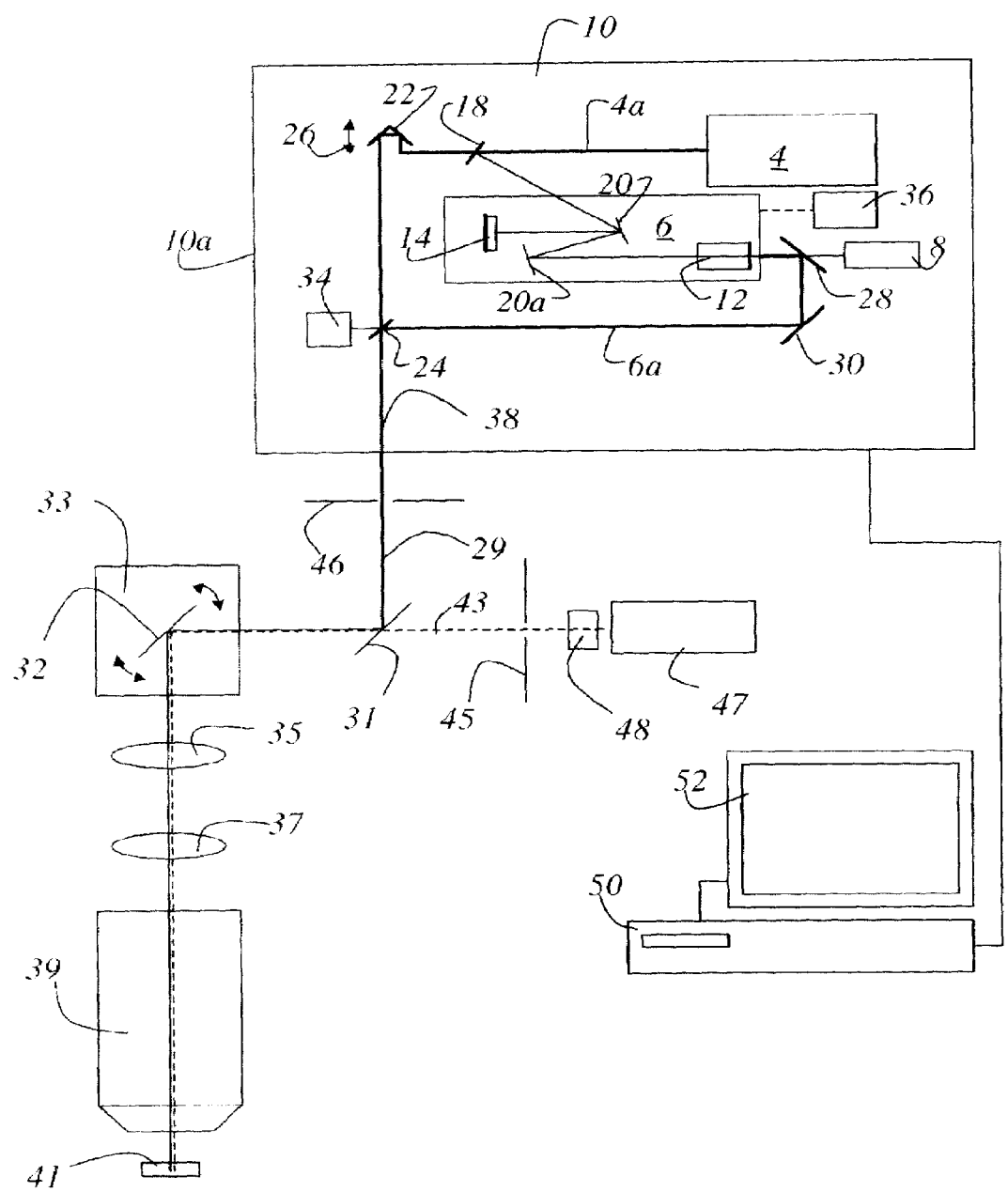
FIG. 2 shows a scanning microscope system according to the present invention, having a light source that is easy to synchronize.

FIG. 2 shows a light source 10 according to the present invention in combination with a scanning microscope. Light source 10 possesses a first laser 4 and a second laser 6. First laser 4 is embodied, in this exemplary embodiment, as a Ti:sapphire laser. Second laser 6 is a Nd:YVO$_4$ laser that is optically pumped by a diode laser 8. The Nd:YVO$_4$ laser encompasses a Nd:YVO$_4$ crystal 12 and a saturable absorber mirror made of a semiconductor material, referred to as a SESAM (semiconductor saturable absorber mirror) 14. For adaptation of the resonator length, at least SESAM 14 can be configured movably. A Fabry-Perot modulator 20 that acts as a deflection mirror, and a further deflection mirror 20a, are provided between Nd:YVO$_4$ crystal 12 and SESAM 14. First laser 4 emits light in a first beam path 4a in which a beam splitter 18 is arranged in such a way that it directs a portion of the light of first laser 4 onto Fabry-Perot modulator 20, specifically in a manner precisely congruent with the impact point of the Nd:YVO$_4$ laser. Fabry-Perot modulator 20 comprises a highly reflective Bragg reflector (reflectivity approx. 97.5%) for the 1064 nm wavelength. The Bragg reflector is made up of a sequence of GaAs/AlAs semiconductor layer pairs that are applied onto a Ga/As substrate. An InGaAs layer is in turn epitaxially applied onto this mirror. The gap between the air/InGaAs transition and the InGaAs/Bragg reflector transition forms a Fabry-Perot resonator. The InGaAs layer is selected in such a way that it is transparent to 1064 nm but not to the wavelengths of the Ti:sapphire laser. The energy band boundary is then typically located at 970 nm.

The resonance frequency and energy band boundary of the Fabry-Perot resonator are temperature-dependent. The temperature is thus selected, by experiment, in such a way that the resonance frequency lies just below 1064 nm (i.e., at a greater wavelength). A temperature control unit 36 is provided for this purpose. Fabry-Perot modulator 20 is therefore no longer transparent to light having a wavelength of 1064 nm. The losses in the Nd:YVO$_4$ laser are then so great that the laser does not oscillate. Using beam splitter 18, a small portion of first laser 4 (also referred to as the "master laser") is then diverted out of first beam path 4a and irradiated onto Fabry-Perot modulator 20 onto the same impact point in the Nd:YVO$_4$ laser beam path. Free charge carriers are then produced in the InGaAs. That results in a phase shift in the Fabry-Perot resonator so that the resonance frequency is shifted to shorter wavelengths. The losses in the ND:YVO$_4$ laser resonator therefore decrease, and the laser oscillates. After passage of the Ti:sapphire laser pulse, a rapid (on the order of 450 ps) recombination of the free charge carriers occurs, and the initial state is then restored. In this fashion, the ND:YVO$_4$ laser can be modulated on the same cycle as the Ti:sapphire laser; this is why the terms "master" and "slave" laser are also used. SESAM 14 ensures that the Nd:YVO$_4$ laser emits mode-coupled radiation. As already mentioned above, the portion of the light of first laser 4 provides external optical modulation. The resonance frequency can be shifted by monitoring and controlling the temperature of Fabry-Perot modulator 20, thereby allowing the working point to be selected. Second laser 6 emits light in a second beam path 6a. The light in first beam path 4a of first laser 4 is delivered onto a deflection unit 22 which can be displaced in the direction of a double arrow 26 so as thereby to adapt the optical path lengths of the light of first and second laser 4 and 6. Provided between second laser 6 and diode laser 8 is a deflection mirror 28 that is embodied as a dichroic mirror and that directs the light of second laser 6 onto a further deflection mirror 30. From deflection mirror 30, the light of the second laser arrives at an optical combining means 24. From optical combining means 24, a portion of the light of first laser 4 and a portion of the light of second laser 6 arrive at a measurement unit 34 for ascertaining cross-correlation, which unit provides information and assistance for setting the synchronization or controlled delay of the laser pulses. A tiny portion of the light of first laser 4 is reflected; a portion of second laser 6 is transmitted. The two beams are together focused, by means of a lens (not depicted), onto a nonlinear crystal, for example BBO (beta-barium borate), that is 1 mm thick. A summed frequency mixing takes place therein (i.e. $\omega_{Ti:Sa}$+ $\omega_{Nd} = \omega_{summed\ frequency}$). $\omega_{summed\ frequency}$ is then located at approx. 472 nm, and is measured with a photomultiplier, the wavelength not being measured being filtered out with filters. A signal is measured only if the pulses of first and second laser 4 and 6 overlap both in time and in space. Light source 10, comprising first laser 4, second laser 6, diode laser 8, displaceable deflection unit 22, optical combining means 24, and measurement unit 34 for ascertaining the cross-correlation, is combined into one module 10a. Module 10a can be flange-mounted onto an optical examination apparatus for microscopic specimens or onto the scanning microscope. A computer 50, equipped with a display 52, is connected to module 10a and to the optical examination apparatus for microscopic specimens or the scanning microscope. Computer 50 serves to monitor the microscope adjustment operations, and to present to a user in graphical or other readable form, on display 52, data relevant to the adjustment process.

As depicted in FIG. 2, combined light beam 38 travels into the confocal microscope. First and second laser 4 and 6 are two ultra-short-pulse lasers, passively synchronized with one another, that are used, together with the corresponding optical means, as light source 10 for multi-photon microscopy, multi-color microscopy, or also for STED microscopy. Light source 10 has the advantage that two completely different lasers (first and second laser 4 and 6) can be synchronized with one another. It is then also possible, for example, to effect two-photon absorption (TPA) using two different photons (each having a different energy) and to generate the second or third harmonic (SHG=second harmonic generation; THG=third harmonic generation) or other mixed processes in the sample using two different lasers, simultaneously or a defined sequential manner. When a neodymium-doped laser, for example a Nd:YVO$_4$ laser, is coupled to a Ti:sapphire laser, the third harmonic can be generated with the ND:YVO$_4$ laser and TPA or SHG can be accomplished with the Ti:sapphire laser. It is also conceivable, however, to synchronize a laser at 1250 nm with a Ti:sapphire laser, as well as other combinations. In the method, the Ti:sapphire laser is in fact also tunable as to wavelength, which of course is an enormous advantage.

For STED and other applications, the lasers could each separately be additionally converted (OPO, white-light generation in a microstructured fiber, frequency conversion, etc.). A universal and high-performance light source, with great flexibility and a variety of possible configurations, is thus obtained.

The various synchronized lasers can then, using time-delay methods, be coordinated with one another in time in controlled fashion, as is necessary for many applications. Additional applications are possible, for example multi-color microscopy, pump-sample experiments, lifetime measurements, FLIM, FSC, and conventional confocal microscopy. The embodiment using a confocal scanning microscope is evident from FIG. 1, so no further discussion thereof is necessary.

The invention has been described with reference to a particular exemplary embodiment. It is self-evident, however, that changes and modifications can be made without thereby leaving the range of protection of the claims below.

PARTS LIST

1 Light source
3 Electromagnetic energy source
4 First laser
4a First beam path
5 Beam splitter
Second laser
6a Second beam path
7 Mirror
8 Diode laser
9 Intermediate element
10 Light source
10a Module
11 Mirror
12 Nd:YVO$_4$ crystal
13 Beam combiner
14 SESAM
16 First beam path
17 Light
18 Beam splitter
19 First partial light beam
20 Fabry-Perot modulator
20a Further deflection mirror
21 Second partial light beam
22 Deflection unit
27 Partial light beam
24 Combining means
25 Optically parametric oscillator (OPO)
26 Double arrow
27 Partial light beam
28 Deflection mirror
29 Illuminating light
30 Deflection mirror
31 Beam splitter
32 Scanning mirror
33 Beam deflection device
34 Measuring unit for ascertaining cross-correlation
35 Scanning optical system
36 Temperature control unit
37 Tube optical system
38 Combined light beam
39 Microscope optical system
41 Sample
43 Detected light
45 Detection pinhole
46 Illumination pinhole
47 Detector
48 Bandpass filter
49 Detector
50 Computer
52 Display
61 Means for influencing focus shape

The invention claimed is:
1. A light source for the illumination of microscopic specimens, comprising:
a first and a second laser wherein each of which emits light into a first beam path and into a second beam path;

an optical combining means being introduced in the first and in the second beam path; and an axially displaceable deflection unit for setting a path length difference between the light of the first and the second laser.

2. The light source as defined in claim 1, wherein both the first laser and the second laser are short-pulse lasers that are passively synchronized with one another.

3. The light source as defined in claim 1, wherein a measurement unit for ascertaining cross-correlation is provided, which receives a portion of the light of the first laser and a portion of the light of the second laser, and is used to ascertain a setting signal for adjusting the synchronization or controlled delay of the laser pulses of the first and/or second laser.

4. The light source as defined in claim 1, wherein the first laser is a Ti:sapphire laser.

5. The light source as defined in claim 1, wherein the second laser is a Nd:YVO$_4$ laser that is optically pumped with a diode laser.

6. The light source as defined in claim 1 wherein the first laser, the second laser, the diode laser, the displaceable deflection unit, the optical combining means, and the measurement unit for ascertaining cross-correlation are combined into one module.

7. The light source as defined in claim 6, wherein the module is flange-mounted onto an optical examination apparatus for microscopic specimens.

8. A scanning microscope system having:
a beam deflection device for guiding an illuminating light beam over a sample,
a microscope optical system,
a detector,
a light source which emits a combined light beam that is generated by a first laser and a second laser; and
an optical combining means which synchronizes the light of the first laser with the light of the second laser; and
a displaceable deflection unit for setting a path length difference between the light of the first and the second laser.

9. The scanning microscope system as defined in claim 8, wherein the first laser defines a first beam path and the second laser a second beam path; and the optical combining means is introduced in the first and in the second beam path.

10. The scanning microscope system as defined in claim 9, wherein the displaceable deflection unit is provided in the beam path of the first laser or of the second laser.

11. The scanning microscope system as defined in claim 10, wherein the light source is equipped with a measurement unit for ascertaining cross-correlation which receives a portion of the light of the first laser and a portion of the light of the second laser, and can be used to ascertain a setting signal for adjusting the synchronization or controlled delay of the laser pulses of the first and/or second laser.

12. The scanning microscope system as defined in claim 8, wherein the first laser of the light source is a Ti:sapphire laser.

13. The scanning microscope system as defined in claim 8, wherein the second laser is a Nd:YVO$_4$ laser that is optically pumped with a diode laser.

14. The scanning microscope system as defined in claim 8, wherein the first laser, the second laser, the diode laser, the displaceable deflection unit, the optical combining means, and the measurement unit for ascertaining cross-correlation are combined into one module.

15. The scanning microscope system as defined in claim 14, wherein a computer that is connected to the module is provided; and the computer has a display on which adjustment data and/or adjustment aids for synchronization of the first and second laser are displayed for the user.

16. The scanning microscope system as defined in claim 8, wherein said displaceable deflection unit is axially displaceable.

* * * * *